United States Patent [19]

Schaldach

[11] Patent Number: 4,867,160
[45] Date of Patent: Sep. 19, 1989

[54] CARDIAC PACEMAKER

[75] Inventor: Max Schaldach, Erlangen, Fed. Rep. of Germany

[73] Assignee: Biotronik Mess- und Therapiegeräte GmbH & Co., Berlin, Fed. Rep. of Germany

[21] Appl. No.: 908,291

[22] Filed: Sep. 17, 1986

[30] Foreign Application Priority Data

Sep. 18, 1985 [DE] Fed. Rep. of Germany ....... 3533597

[51] Int. Cl.⁴ ............................................. A61N 1/36
[52] U.S. Cl. ............................................. 128/419 PG
[58] Field of Search ................................ 128/419 PG

[56] References Cited

U.S. PATENT DOCUMENTS 4,303,075 12/1981 Heilman et al. ................. 128/419 D

FOREIGN PATENT DOCUMENTS 48505 5/1985 European Pat. Off. ..... 128/419 PG
140472 5/1985 European Pat. Off. ..... 128/419 PG Primary Examiner—William E. Kamm
Attorney, Agent, or Firm—Spencer & Frank

[57] ABSTRACT

A cardiac pacemaker having circuitry for varying the pacing rate, in accordance with a signal recorded in the patient's body and correlated with the stroke volume, in which for automatic adaptation of the functional dependency of the pacing rate on the value correlated with the stroke volume at the maximum allowable or expected physical exertion on the part of the patient, the pacing rate is varied in a range adapted to this exertion; as a reference point for the functional dependency, the particular rate is associated with the particular stroke volume at which the product of the stroke volume and the pacing rate is a maximum.

6 Claims, 3 Drawing Sheets

CARDIAC PACEMAKER

BACKGROUND OF THE INVENTION

The invention relates to a cardiac pacemaker having a circuit arrangement for varying the pacing rate as a function of a measured value representing the stroke volume as recorded in the patient's body.

A pacemaker of this type is known from European Pat. No. (A) 00140 472. In a pacemaker of this type, it is difficult to optimize the setting of the heart rate for a given patient as a function of a value corresponding to the stroke volume, because cardiac characteristics vary individually from patient to patient.

For precise matching of pacemaker behavior to the individual, the nonlinear relationship between the cardiac output, the stroke volume, the heart rate and the load on the heart must be known, and a characteristic control curve or a regulating range must be selected. Cardiac behavior, and in particular the suitability of the stroke volume in the vicinity of the load limit as a control criterion, cannot be predicted. Numerous experiments have accordingly been necessary, to attain a suitable setting.

SUMMARY OF THE INVENTION

Since point-by-point testing and setting of the operating range is relatively tedious, it is the object of the invention to provide an apparatus with which the functional dependency of the heart frequency on the stroke volume can be optimized in a simple manner and tested periodically as needed.

This object is attained by a cardiac pacemaker having a circuitry arrangement for varying the pacing rate as a function of a measured value representative of the stroke volume, the circuitry arrangement having first and second operating states, a multiplier for multiplying the value of the stroke volume by the value of the pacing, rate and a recognizing circuitry arrangement for recognizing a particular value of the product formed by the multiplier.

The invention is based in particular on the recognition that calibration is easily attainable in the range of relatively major physical exertion, because the limit of adaptability means that the stroke volume does not vary any further, and so the exertion itself need not be known precisely, nor need it be ascertained by measurement apparatus.

A particularly advantageous feature is that in the normal situation, point-by-point detection of the heart rate as a function of the cardiac output can be dispensed with when such a pacemaker is being set in the major exertion range. This feature is substantially easier for the patient. Nor is an ergometer or a similar instrument necessary, such as are required when a stress EKG is made. In a favorable manner, the apparatus can even be embodied such that an automatic adaptation to changing circumstances, in terms of cardiac behavior and life situations, is made at regular intervals. In particular, the inventive system keeps pace with improvement in functional capacity. Nevertheless, monitoring and resetting can also by done by the attending physician, who is aided in diagnosis by the trend in the intervening automatic changes that have taken place.

BRIEF DESCRIPTION OF THE DRAWINGS

Advantageous further embodiments of the invention will be described below in detail, along with the description of the preferred embodiment, taken in conjunction with the drawings which include.

DETAILED DESCRIPTION OF THE PREFERRED INVENTION

Figure 1:
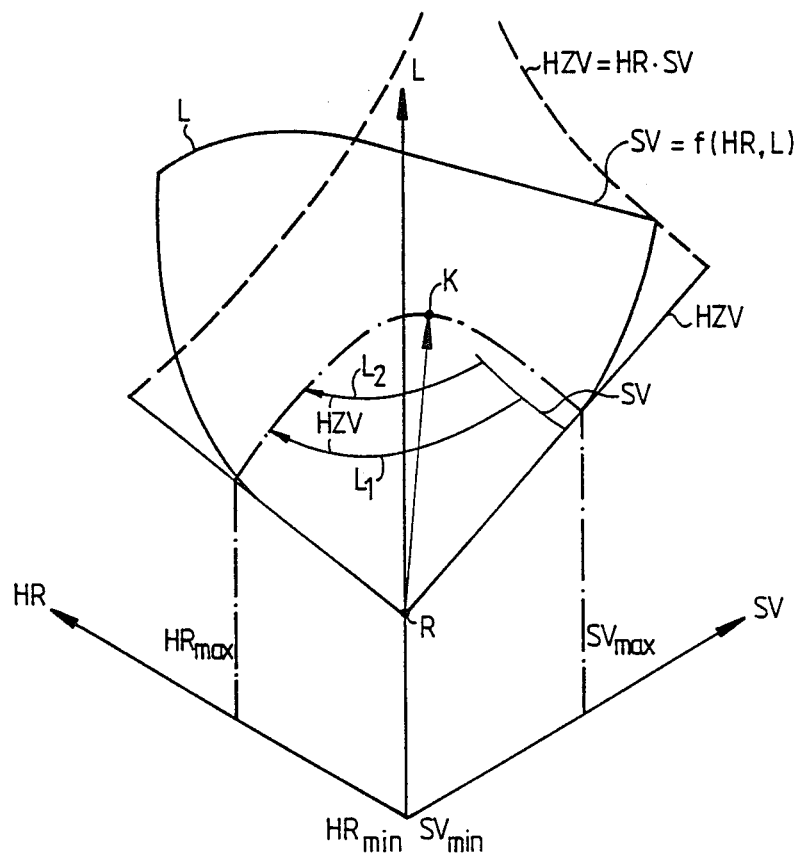
FIG. 1 is a perspective drawing illustrating the function of a pacemaker controlled by stroke volume.

FIG. 1 is an illustration in the form of a graph showing the cardiac output (HZV) as a function of the heart rate and stroke volume. This functional relationship is particularly significant for controlling the pacemaker, because cardiac output is a measure of the functional capacity of the heart, and the variation in heart rate is not an adequate criterion if the attainable stroke volume is not taken into consideration. The cardiac output diagram shows the purely mathematical relationship which is obtained computationally by multiplication. The stroke volume is variable between the minimum and maximum rate, and the same applies to the heart rate. With the pacemaker, however, only the heart rate can be influenced, while the stroke volume adjusts automatically in accordance with the existing capacity of the heart for adaptation. Thus on the one hand, the stroke volume, along with the heart rate, provides a measure of present functional capacity of the heart, while on the other hand a decrease or increase with respect to a constant heart rate provides a criterion indicating that the internal regulating system of the body is seeking an increase or decrease in cardiac output, as long as a particular patient does still have this capacity for adaptation.

In FIG. 1 the dependency of the stroke volume (SV) on the heart rate and load (L) is also illustrated on the same graph to make comparison easier. As FIG. 1 shows, the stroke volume is limited approaching values thereof if cardiac adaptability is restricted, while at higher heart rate or frequency values the stroke volume decreases because the chamber filling decreases. By comparison of the two diagrams, the operating range of the pacemaker can be defined, on the assumption that the load may not deviate substantially from the cardiac output if the functional capacity of the heart is to be satisfactory for the load over a relatively long term.

It is accordingly apparent that excessively raising the heart rate or frequency (as shown by the characteristic curve having a slight slope with respect to the axis HR) leads to a drop in cardiac output and is therefore unfavorable in the present instance. Conversely, the plotted course of a characteristic curve is favorable where the load on a given patient has to remain limited because of the patient's restricted volumetric (stroke volume SV) adaptation. If the family of curves according to FIG. 1 conversely takes a course toward higher frequencies HR - as shown in broken lines - then the operating characteristic curve can be selected flatter; toward higher heat frequencies a range in which the cardiac output is correspondingly increased without a reduction of the stroke volume is attainable. The apparatus according to the invention takes these factors into account.

The exemplary embodiment according to the invention will now be explained in terms of the block diagram of FIG. 2, referring to the diagram of FIG. 3 as needed.

Figure 2:
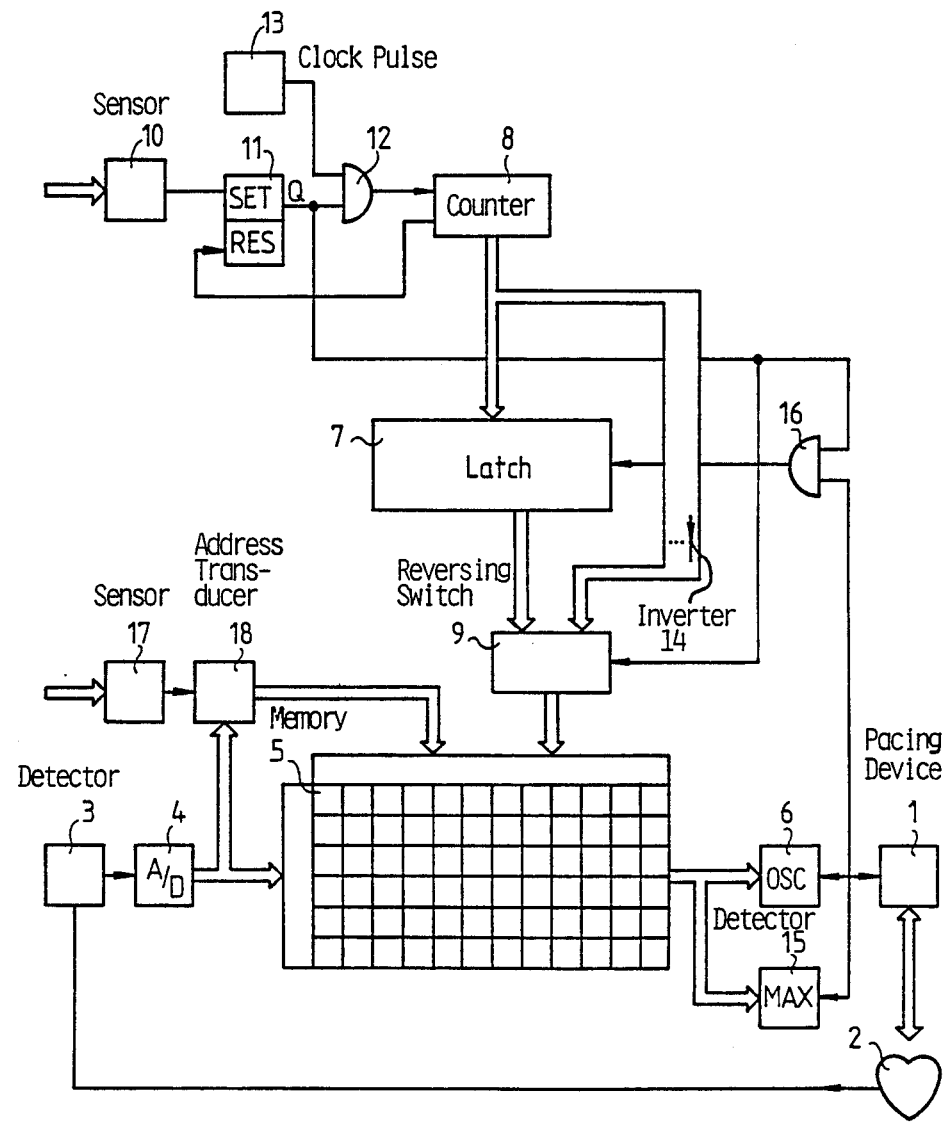
FIG. 2 is a preferred exemplary embodiment according to the invention, shown in as a block diagram.

In FIG. 2, a conventional pacing device is provided, which interacts with a heart 2 which is schematically represented. The pacemaker has the known provisions that prevent the pacing pulses from competing with the heart's own actions. Additionally, a sensor for a value correlated with the stroke volume, such as can be obtained by electroplethysmography for example, is provided. A corresponding detector 3 triggers an analog/digital converter 4, the output signal of which addresses a matrix-organized memory 5. In the case of a typical memory structure—for example in connection with a microprocessor system—the output signal of the analog/digital converter 4 forms a data word addressing a larger memory area. In normal operation, associated frequency values are read out as a result of the alternating digitized ventricle volume values, and these frequency values influence the frequency of a digitally triggerable oscillator. The oscillator 6 dictates the basic rate of the pacemaker, and in the case of a demand pacemaker is resettable by the heart's own actions, so that it defines the escape interval of the pacemaker.

Figure 3:
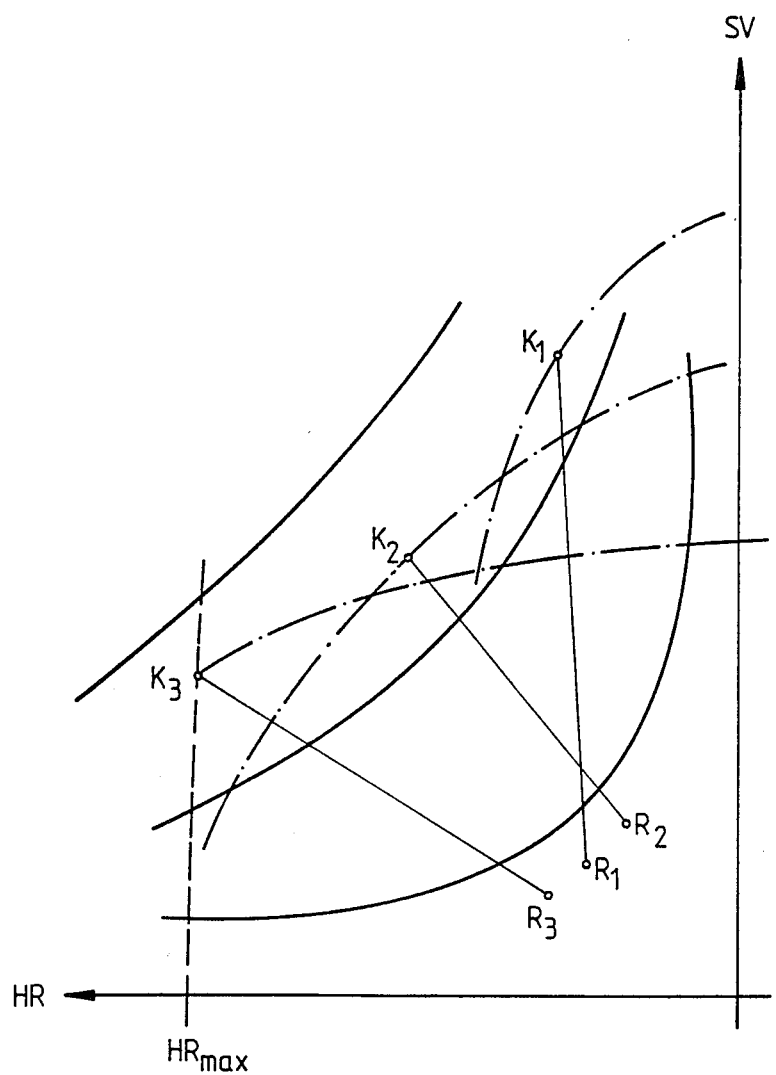
FIG. 3 is a graphical representation of the results of operation of the exemplary embodiment.

The values stored in memory determine an operating characteristic curve, which preferentially forms a straight line and in the diagram of FIG. 3, in which the relationship between the heart rate (HR) and stroke volume (SV) is shown, forms one of the straight lines $K_1-R_1$ to $K_3-R_3$. In the diagram of FIG. 3, various values for the cardiac output (HR x SV) are shown in the form of branches of a hyperbola, with the cardiac output increasing from the origin of the coordinates. The connections K-B may also exhibit a curvature, if such a course appears favorable for therapeutic reasons.

The reversal of the various curves is effected, in the exemplary embodiment shown in FIG. 2, by means of a further partial address, which is contained in a latch 7. This latch is triggered by a counter 8, which is normally in repose. The output signal of the latch 7, as an address signal, proceeds to a reversing switch 9, which in its activated position is also capable of direct switching of the output signal of the counter 8, to address the memory 5. However, as noted, in the normal operating state, the memory region is addressed by the output signal of the latch 7.

Calibration, that is, resetting of the operating characteristic curve, is performed in the exemplary embodiment of the invention whenever the patient's physical exertion is so great that no further stroke volume adaptation in the direction of an increase in volume can take place (steep portion of the surface L in FIG. 1).

Since toward higher heart frequencies the stroke volume additionally decreases because of the decreasing ventricle filling, the dependency of the stroke volume and heart rate no longer follows the course of one of the hyperbola branches—which would mean that the cardiac output would remain constant, in an adaptation to the instantaneous physical exertion—but instead follows a curve that is more or less equivalent to one of the curves that are curved oppositely to the hyperbola, through the points $B_1$ to $K_3$.

In order to make the greatest possible cardiac output available to the patient during major exertion, the operating characteristic curve for the case of major physical exertion on the part of the patient is located with the apparatus according to the invention such that its end point for the case of major exertion, i.e. load on the heart (L), is associated with the largest possible cardiac output, so that by varying the heart frequency in an adaptation to the stroke volume, maximum functional capacity of the heart is assured. The variation of the heart rate is limited by the upper allowable frequency.

Thus if the patient reaches the upper expected exertion level, then a first exertion sensor 10 becomes active and emits an output signal. The exertion sensor 10 preferably comprises a sensor for the blood temperature or for the respiration rate and is digitally adjusted to a predetermined threshold value, which may optionally be variable by external circuitry. In a programmable pacemaker, the output signal of the exertion sensor can correspondingly also be input actively by programming means, so that the calibration can be performed while being monitored by a physician. In an existing exertion sensor for an upper major exertion value, pacemaker adaptation to cardiac behavior takes place automatically, however. The threshold value of the exertion transducer, conversely, is preferably once again adaptable on an individual-patient basis by external programming means.

The activation of the sensor 10 triggers the emission of a pulse, which sets a flip-flop 11, triggering the calibration state. With the output signal Q of the flip-flop 11, and AND gate 12 is connected through, allowing the clock signal of a clock 13 to pass through to the counter 8, which now runs through one counting cycle. The signal Q also actuates the reversing switch 9, so that the output signal of the counter 8 now addresses the memory region 5 directly. Since the most significant bit of the partial address formed by the counter 8 is inverted by an inverter 14, an intervention is made to another region of the memory 5, but in this case the further partial address is emitted by the analog/digital converter 4, so that locations in memory are now addressed as a function of the position of the counter 8 and analog/digital converter 4. These memory locations each contain a frequency value, so that with the passage through the counter, the frequency range, which corresponds to the major exertion on the part of the patient, is addressed and slowly run through. With the matrix-like organization of the memory, selected for purposes of illustration, various columns in the matrix are accordingly addressed with the cycling of the counter; all the memory locations of one column contain the same value for triggering the oscillator 6 (in another preferred exemplary embodiment, the digital value triggering the oscillator may also be derived from the output address of the counter 8 by means of a corresponding conversion during the calibration operation, whereupon the address input of the counter 6 must be reversed accordingly during the calibration operation).

Each addressed memory location also contains a value corresponding to the instantaneous cardiac output (the product of HR and SV), and this value is delivered to a maximum detector 15. This maximum detector emits an output pulse whenever a new valve is greater than the former value. In the case of calibration operation, the output signal from the maximum detector 15 is allowed to pass through to the latch 7 through by an activated subcomponent 16, so that—if in varying the heart frequency a larger value for the output volume at that time is found—the associated counter status is stored in memory in the latch 7. Once the test cycle has been run through completely, the counter 8, upon attaining its original status, emits a pulse which resets the flip-flop 11 to its original state. The search run is then completed and results in storing in memory in the latch 7 of the partial address of the characteristic curve that is associated with the point that assures maximum cardiac output for the patient in the event of major exertion. The operating characteristic curve is preferably selected such that the operating point ascertained for the case of major exertion forms the end point of the operating characteristic curve.

The exemplary embodiment shown represents only one possibility for realization; the corresponding course of the operating characteristic curve can also be ascertained by suitable mathematical operations. This is also true for the operating characteristic curve. In the exemplary embodiment, this was done in table form, for ease of illustration, and this has advantages if the operating characteristic curves are not intended to be straight lines but should instead have an arbitrarily curved course.

It will be appreciated that in the test cycle, the counter for the experimental variation of the heart frequency triggers only heart frequency values that do not drop below a (programmable) allowable frequency limit for the patient. If at this frequency there is not yet any drop in stroke volume during major exertion, then the maximum frequency forms the value that is established at maximum stroke volume and major exertion.

The end of the straight operating lines that correspond to the resting stage is also programmable. By means of a second sensor for exertion 17, an output signal can be emitted—optionally automatically—whenever the patient is at rest, which can be recognized by the pacemaker by means of acceleration detectors and the like. The output signal of the sensor 17 can also be generated by the physician, however, using external programming means.

In this manner, the stroke volume that is established in the state of rest is associated with the specified resting rate. The frequency adaptation dependent on stroke volume is thus "self-calibrating" for the resting range as well, so that fluctuations in the measured value of the stroke volume sensor are compensated for. In the resting range, however, a fixed pacing rate is specified.

By means of the detector 17—after the stroke volume associated with the selected frequency has been established—an address transducer 18 is activated, which by variation of a further partial address of the total address word that addresses the memory 5 specifies that in the state of repose a predetermined pacing rate is adhered to. By addressing the particular memory region of the memory 5, that curve of all the operating characteristic curves leading through the previously ascertained point K that also leads through the now-located point R in the case of repose is selected. (This operation can also be performed by software, using a suitable program.)

In this manner, the stroke volume that is established in the state of rest is associated with the specified resting rate. The frequency adaptation dependent on stroke volume is thus "self-calibrating" for the resting range as well, so that fluctuations in the measured value of the stroke volume sensor are compensated for. In the resting range, however, a fixed pacing rate is specified.

In its realization, the invention is not limited to be above-described example. Instead, many variants are conceivable, which utilize the above concept even with fundamentally different equipment. For instance, it may also be favorable to ascertain a sequence of measured value pairs for the pacing rate and stroke volume in accordance with the aforementioned criterion of maximizing the cardiac output and to interpolate an operating characteristic curve. In this manner, in the stroke-volume-controlled rate adaptation a pair of values for stroke volume and pacing rate that corresponds most closely to exertion requirements will always be established.

The realization is in particular not limited to realization with discrete logic components; instead, it can advantageously also be realized with programmed logic, in particular using a microprocessor.

I claim:

1. A cardiac pacemaker for stimulating the heart of a patient, comprising:

pacing means for applying stimulating pulses to the heart of the patient at a rate determined by a pacing parameter;

first measured value pickup means for detecting a first attribute of a patient's body representative of the cardiac stroke volume and producing a first output signal representative of said first attribute;

circuitry means for varying the pacing parameter as a function of said first output signal as an input variable and which are correlated with physical exertion of the patient's body, said circuitry means being changeable between a first operating state and a second operating state;

means for cycling the pacing parameter through a pacing rate interval during physical exertion of the patient while in said first operating state, wherein said pacing rate interval is determined according to the physical exertion, means for supplying a second signal which is representative of a current value of the pacing rate; said circuitry means determining a product of the value of said first output signal representative of the stroke volume and said second signal which is representative of the current value of the pacing rate, said product representing cardiac output;

recognition means for determining the maximum value of said product; and memory means responsive to recognition by said recognition means of the maximum value of said product for storing at least one pair of values of the pacing rate and the value of said first output signal representative of the stroke volume corresponding to said maximum value of said product determined by said recognition means;

wherein in said second operating state said pacing means supplies pacing signals at a rate corresponding to that stored in said memory means.

2. A cardiac pacemaker as defined in claim 1, wherein a plurality of pairs of values are stored in said memory means which are representative of points on a characteristic operating curve which associates one value of the pacing rate with one value at a time of said first output signal representative of the stroke volume.

3. A cardiac pacemaker as defined by claim 2, wherein for an exertion status corresponding to physical repose by the patient, said circuitry means determines a correspondingly low pacing rate which corresponds to the value of said first output signal the stroke volume stored in said memory means.

4. A cardiac pacemaker as defined by claim 3, wherein said circuitry means determines a characteristic operating curve by interpolation between the pairs of values associated with exertion and with physical repose.

5. A cardiac pacemaker as defined by claim 1, further comprising an exertion sensor which, during said first operating state, upon attaining a specified value emits a signal to said circuitry means which in response to said signal from said exertion sensor changes the operating state from said first operating state to said second operating state.

6. A cardiac pacemaker as defined by claim 1, wherein said circuitry means is changeable from said first operating state to said second operating state by an external programming means.

* * * * *